United States Patent [19]

Yamamoto et al.

[11] Patent Number: 4,631,347
[45] Date of Patent: Dec. 23, 1986

[54] DITHIOLPHOSPHORIC ACID ESTERS

[75] Inventors: Haruyasu Yamamoto, Takarazuka; Kiyoshi Kasamatsu, Toyonaka; Takayuki Okabe, Nishinomiya; Kunio Mukai, Osaka, all of Japan

[73] Assignee: Sumitomo Chemical Company, Limited, Osaka, Japan

[21] Appl. No.: 542,709

[22] Filed: Oct. 17, 1983

[30] Foreign Application Priority Data

Oct. 25, 1982 [JP] Japan .................. 57-188004

[51] Int. Cl.$^4$ ............................. C07F 9/165
[52] U.S. Cl. ...................................... 558/208
[58] Field of Search .................. 260/963; 558/208

[56] References Cited

U.S. PATENT DOCUMENTS 3,725,546  4/1973  Tsuchiya et al. ............. 424/225
4,273,769  6/1981  Koyanagi et al. ............. 260/963
4,383,991  5/1983  Gough ........................... 260/963

*Primary Examiner*—Anton H. Sutto
*Attorney, Agent, or Firm*—Stevens, Davis, Miller & Mosher

FOREIGN PATENT DOCUMENTS 141496  11/1980  Japan.

[57] ABSTRACT

A dithiolphosphoric acid ester of the formula,

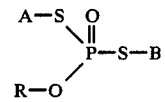

wherein R is methyl or ethyl group, and when R is methyl group, A is iso-butyl, sec-butyl or tert-butyl group and B is methyl, ethyl or n-propyl group, when R is ethyl group and A is sec-butyl or tert-butyl group, B is methyl group, and when R is ethyl group and A is iso-butyl group, B is methyl, ethyl or n-propyl group, which is useful as a soil pesticidal composition for pests in soil.

1 Claim, No Drawings

DITHIOLPHOSPHORIC ACID ESTERS

The present invention relates to a dithiolphosphoric acid ester of the formula (I) (hereinafter referred to as present compound),

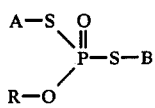 (I)

wherein R is methyl or ethyl group, and when R is methyl group, A is iso-butyl, sec-butyl or tert-butyl group and B is methyl, ethyl or n-propyl group, when R is ethyl group and A is sec-butyl or tert-butyl group, B is methyl group, and when R is ethyl group and A is isobutyl group, B is methyl, ethyl or n-propyl group, its production and soil pesticidal compositions containing it as an active ingredient.

That some kinds of dithiolphosphoric acid ester, for example, trimethyl dithiolphosphate, O-ethyl S,S-di-n-butyl dithiolphosphate, etc., can be used as an active ingredient for insecticides, acaricides and nematocides, is described in the specification of Dutch Pat. No. 261789 (U.S. Pat. No. 3,309,371) and Japanese Patent Publication No. 29487/1969. But, it may not always be said that these compounds are always satisfactory as an active ingredient for soil pesticidal compositions.

The present inventors found that the present compound has a sufficient controlling activity against pests living in soil and doing damage to paddy rice, vegetables, flowers and ornamental plants, lawn grasses, fruit trees, tea, mulberry and the like, and besides that said compound gives no such phytotoxicity as to become a problem to these plants.

The soil pest includes for example pests of Diabrotica genus such as western corn rootworm (*Diabrotica virgifera* Le Conte), northern corn rootworm (*Diabrotica longicornis* Say), southern corn rootworm (*Diabrotica undecimpunctata howardi* Barber), etc., pests of Anomala genus such as cupreous chafer (*Anomala cuprea* Hope), soybean beetle (*Anomala rufocuprea* Motschulsky), cherry chafer (*Anomala daimiana* Harlod), striated chafer (*Anomala testaceips* Motschulsky), etc., pests of Popillia genus such as Japanese beetle (*Popillia japonica* Newman), etc., pests of Aulacophora genus such as cucurbit leaf beetle (*Aulacophora femoralis* Motschulsky), etc., pests of Phyllotreta genus such as striped cabbage flea beetle (*Phyllotreta vittata* Fabricius), etc., pests of Melanotus genus such as sweetpotato wireworm (*Melanotus caudex* Lewis), etc., pests of Agriotes genus such as barley wireworm (*Agriotes fuscicollis* Miwa), etc., pests of Hylemya genus such as onion maggot (*Hylemya antiqua* Meigen), turnip maggot (*Hylemya floralis* Fallén), seedcorn maggot (*Hylemya platura* Meigen), etc., pests of Agrotis genus such as common cutworm (*Agrotis segetum* Denis et Schiffermüller), black cutworm (*Agrotis ipsilon* Hufnagel), etc., pest of Gryllotalpa genus such as African mole cricket (*Gryllotalpa africana* Palisot de Beauvois), etc., pests of Lissorhoptrus genus such as ricewater weevil (*Lissorhoptrus oryzophilus* Kuschel), etc., pests of Pratylenchus genus such as Cobb root-lesion nematode (*Pratylenchus penetrans* Cobb), walnut root-lesion nematode (*Pratylenchus vulnus* Allen et Jensen), coffee root-lesion nematode (*Pratylenchus coffeae* Zimmermann), etc., pests of Heterodera genus such as soybean cyst nematode (*Heterodera glycines* Ichinohe), etc., pests of Meloidogyne genus such as northern root-knot nematode (*Meloidogyne hapla* Chitwood), cotton root-knot nematode (*Meloidogyne incognita* var. *acrita* Chitwood), Javanese root-knot nematode (*Meloidogyne javanica* Treub), peanut root-knot nematode (*Meloidogyne arenaria* Neal), etc., pests of Aphelenchoides genus such as rice whitetip nematode (*Aphelenchoides besseyi* Christie) and the like. The present compound has excellent controlling activity, particularly, against pests belonging to Diabrotica, Anomala and Meloidogyne genera.

Consequently, the present compound can be used as an active ingredient in soil pesticidal compositions which can be employed for paddy field, plowland, flower garden, orchard, pasture, turf, tea garden, mulberry farm and the like.

The present compound can be produced by reacting a thiophosphoric acid halide of the formula (II),

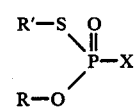 (II)

wherein R' is A or B, A, B and R are as defined above, and X is halogen atom,
with 1 to 5 equivalents of an alkylmercaptan of the formula (III),

R"SH (III)

wherein R" is B when R' is A and it is A when R' is B, and A and B are as defined above,
at the vicinity of $-10°$ to about 50° C. for about 0.5 to about 5 hours in a solvent or without a solvent in the presence of 1 to 1.5 equivalents of a dehydrohalogenating agent and a phase transfer catalyst or copper catalyst.

The solvent includes for example ketones (e.g. acetone, methyl ethyl ketone, methyl isobutyl ketone, cyclohexanone), halogenated hydrocarbons (e.g. chloroform, carbon tetrachloride, dichloroethane, chlorobenzene, dichlorobenzene), aromatic hydrocarbons (e.g. benzene, toluene, xylene), nitriles (e.g. acetonitrile, isobutyronitrile), water and mixtures thereof.

The dehydrohalogenating agent includes for example organic bases such as pyridine, triethylamine, N,N-diethylaniline, etc., and inorganic bases such as sodium hydroxide, potassium hydroxide, sodium carbonate, potassium carbonate, etc. The phase transfer catalyst includes for example tetraalkylammonium halides such as tetrabutylammonium bromide, triethylbenzylammonium chloride, etc., and the copper catalyst includes for example copper powder, cuprous chloride, etc.

After completion of the reaction, aftertreatment is carried out as usual, and if necessary, the product obtained is purified by chromatography, distillation and the like.

Also, the present compound can be produced by reacting a dithiophosphoric acid salt of the formula (IV),

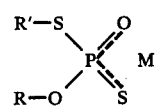 (IV)

wherein R and R' are as defined above, and M is an alkali metal atom, with 1 to 10 equivalents of an aklyl halide of the formula (V), $$R''-Y \qquad (V)$$

wherein R" is as defined above and Y is halogen atom, at the vicinity of 20° to about 80° C. for about 0.5 to about 3 hours in a solvent or without a solvent.

The solvent includes, in addition to the foregoing ketones, nitriles, water, etc., alcohols (e.g. methanol, ethanol, isopropanol, tert-butanol, methyl cellosolve) and mixtures thereof.

After completion of the reaction, aftertreatment is carried out in the same manner as above, and the product obtained is purified if necessary.

Next, production examples for the present compound will be shown.

PRODUCTION EXAMPLE 1

[production of the present compound (4)]

12.6 Grams of potassium O-ethyl S-tert-butyl phosphorodithioate was dissolved in 50 ml of acetone, and after adding 9.4 g of methyl iodide, the mixture was refluxed for 30 minutes with stirring. After completion of the reaction, acetone was removed under reduced pressure, and toluene was added to the residue. The mixture was washed with 3% aqueous sodium hydrogencarbonate and then with water, and toluene was removed under reduced pressure to obtain 9.1 g of a pale yellow and oily O-ethyl S-methyl S-tert-butyl phosphorodithiolate as a residue.

$n_D^{21.7} 1.5102$

PRODUCTION EXAMPLE 2

[production of the present compound (8)]

To a solution of 8.8 g of O-ethyl S-methyl phosphorochloridothioate in 15 ml of toluene were added 5.4 g of isobutylmercaptan and a catalytic amount of tetrabutylammonium bromide. Thereafter, 4.6 g of 50% aqueous sodium hydroxide solution was added dropwise over 1 hour with stirring while cooling the reaction mixture so that the inner temperature was 0° to 10° C. After completion of the addition, the reaction mixture was stirred at room temperature for further one hour. After completion of the reaction, the reaction mixture was washed with 3% aqueous sodium hydroxide and then with water, and toluene was removed under reduced pressure. The oily product obtained as a residue was purified by column chromatography on silica gel to obtain 7.5 g of a pale yellow and oily O-ethyl S-methyl S-iso-butyl phosphorodithiolate.

$n_D^{21.6} 1.5068$

Examples of the present compound which can be produced by the foregoing method are shown in Table 1.

TABLE 1

Dithiolphosphoric acid ester of the formula:

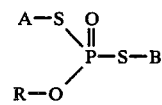

| Compound No. | A | B | R | Physical constant | |
|---|---|---|---|---|---|
| (1) | tert-C₄H₉ | CH₃ | CH₃ | $n_D^{21.2}$ | 1.5168 |
| (2) | " | C₂H₅ | " | $n_D^{20.0}$ | 1.5116 |
| (3) | " | n-C₃H₇ | " | $n_D^{20.0}$ | 1.5058 |
| (4) | " | CH₃ | C₂H₅ | $n_D^{21.7}$ | 1.5102 |
| (5) | iso-C₄H₉ | CH₃ | CH₃ | $n_D^{21.1}$ | 1.5140 |
| (6) | " | C₂H₅ | " | $n_D^{23.0}$ | 1.5020 |
| (7) | " | n-C₃H₇ | " | $n_D^{21.7}$ | 1.5077 |
| (8) | " | CH₃ | C₂H₅ | $n_D^{21.6}$ | 1.5068 |
| (9) | " | C₂H₅ | " | $n_D^{21.6}$ | 1.5027 |
| (10) | " | n-C₃H₇ | " | $n_D^{25.6}$ | 1.4993 |
| (11) | sec-C₄H₉ | CH₃ | CH₃ | $n_D^{22.0}$ | 1.5106 |
| (12) | " | C₂H₅ | " | $n_D^{22.0}$ | 1.5058 |
| (13) | " | n-C₃H₇ | " | $n_D^{22.0}$ | 1.5035 |
| (14) | " | CH₃ | C₂H₅ | $n_D^{28.0}$ | 1.5224 |

When the present compounds are used as an active ingredient for soil pesticidal compositions, they are generally formulated into oil sprays, emulsifiable concentrates, wettable powders, granules, dusts, aerosols, etc. by mixing with a solid, liquid or gaseous carrier and if necessary, adding auxiliaries for formulation such as surface active agents and others.

These compositions contain 0.1 to 99.9% by weight, preferably 1 to 80% by weight of the present compound as an active ingredient.

The solid carrier includes for example fine powders or granules of clays (e.g. kaolin, diatomaceous earth, white carbon, Fubasami clay, bentonite, terra abla), talcs, other inorganic minerals (e.g. sericite, quartz powder, sulfur powder, activated carbon, calcium carbonate, hydrated silica), chemical fertilizers (e.g. ammonium sulfate, ammonium phosphate, ammonium nitrate, urea, ammonium chloride) and the like. The liquid carrier includes for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexane, kerosene, petroleum ether), esters (e.g. ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride) and the like.

The gaseous carrier, i.e. propellant, includes for example freon gas, butane gas, carbon dioxide gas and the like.

The surface active agent includes for example alkyl sulfates, alkylsulfonates, alkylarylsulfonates, alkyl aryl ethers and their polyoxyethylenized products, polyethylene glycol ethers, polyhydric alcohol esters, sugar alcohol derivatives and the like.

The fixing agent and dispersing agent include for example casein, gelatin, polysaccharides (e.g. starch powder, gum arabic, celllulose derivatives, alginic acid), lignin derivatives, bentonite, saccharide, synthetic water-soluble polymers (e.g. polyvinyl alcohol, polyvinyl pyrrolidone, polyacrylic acids) and the like.

The stabilizer includes for example PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, surface active agents, fatty acids and their esters, and the like.

Next, formulation examples for the present compound will be shown.

The present compound is shown by Compound No. in Table 1.

FORMULATION EXAMPLE 1

Emulsifiable concentrate

To forty parts of each of the present compounds (1) to (14) are added 50 parts of xylene and 10 parts of Sorpol SM-200, an emulsifier (mixture of alkylphenol and dodecylbenzenesulfonic acid), and the mixture is well mixed by stirring to obtain a 40% emulsifiable concentrate of each compound.

FORMULATION EXAMPLE 2

Wettable powder

To forty parts of each of the present compounds (1) to (14) is added 5 parts of Sorpol SM-200, an emulsifier, and the mixture is well mixed. Thereafter, 20 parts of Carplex #80 (synthetic hydrated silicon oxide fine powder) and 35 parts of 300-mesh diatomaceous earth are added, and the mixture is well mixed by stirring on a juice mixer to obtain a 40% wettable powder of each compound.

FORMULATION EXAMPLE 3

Granule

To five parts of each of the present compounds (1) to (14) are added 5 parts of Toyolignin CT (ligninsulfonate) and 90 parts of GSM clay (quartz powder), and the mixture is well mixed by stirring on a mortar. Thereafter, to the mixture is added water corresponding to 10% thereof, and the resulting mixture is further stirred, granulated on a granulator and air-dried to obtain a 5% granule of each compound.

FORMULATION EXAMPLE 4

Dust

To 5 parts of each of the present compounds (1) to (14) are added 20 parts of acetone, 3 parts of Carplex #80, 0.3 part of PAP (isopropyl acid phosphate) and 91.7 parts of 300-mesh talc. The mixture is well mixed by stirring on a juice mixer, and acetone is removed by evaporation to obtain a 5% dust of each compound.

FORMULATION EXAMPLE 5

Oil spray

To 20 parts of each of the present compounds (1) to (14) is added 80 parts of kerosene, and the mixture is well mixed to obtain a 20% oil spray of each compound.

These compositions, as such or after diluted with water, are applied to soil surface by spraying the aqueous dilute liquors or scattering the dusts or granules, or used for drenching soil, and after spraying, they are mixed with soil or foliar-sprayed. Also, they may be used in mixtures with other insecticides, acaricides, nematocides, fungicides, seed disinfectants, fertilizers or soil improvers, or may be used at the same time together with these chemicals without mixing.

When the present compounds are used as an active ingredient for soil pesticidal compositions, the dosage rate is generally 10 to 1000 g/10 ares, preferably 50 to 500 g/10 ares, and the application concentration is 0.01 to 30% when the emulsifiable concentrate or wettable powder is diluted with water.

These dosage rate and application concentration vary with the form of composition, application time, application scene, application method, kind of soil pest, degree of damage and other conditions, so that they may be increased or decreased independently of the foregoing ranges.

Next, the controlling activity of the present compounds against soil pests will be shown with reference to the following test examples. Unless otherwise stated, a three-replication test was employed in every test example.

Of the test compounds, the present compounds and compounds used as control were shown by Compound No. in Table 1 and that in Table 2, respectively.

TABLE 2

| Compound No. | Chemical formula | Remark |
| --- | --- | --- |
| (A) | $n\text{-}C_3H_7S\diagdown\underset{C_2H_5O}{\overset{}{P}}\diagup\overset{O}{\diagdown}S\text{-}n\text{-}C_3H_7$ | ethoprophos |
| (B) | $CH_3S\diagdown\underset{CH_3O}{\overset{}{P}}\diagup\overset{O}{\diagdown}SCH_3$ | Compound described in the specification of Dutch Patent No. 261789 (U.S. Pat. No. 3,309,371) |
| (C) | $n\text{-}C_4H_9S\diagdown\underset{C_2H_5O}{\overset{}{P}}\diagup\overset{O}{\diagdown}S\text{-}n\text{-}C_4H_9$ | Compound described in Japanese Patent Publication No. 29847/1969 |

TEST EXAMPLE 1

The emulsifiable concentrate of each test compound formulated according to Formulation example 1 was diluted with water, and 10 ml of the resulting aqueous dilute liquor was mixed with 50 g of soil (24 mesh) to make the concentration of active ingredient in soil 1.2 ppm. The soil was then placed in a polyethylene cup of 5.6 cm in diameter and 5.8 cm high, and two pieces of corn having roots of 2 to 3 cm long were planted. At the same time, ten third instar larvae of southern corn rootworm (*Diabrotica undecimpunctata howardi* Barber) were liberated in the cup.

Two days after liberation, the number of the dead and alive of the larvae was examined to obtain mortality (%). The result is shown in Table 3.

TABLE 3

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (A) | 90 |
| (B) | 0 |
| (C) | 0 |

TABLE 3-continued

| Test compound | Mortality (%) |
| --- | --- |
| No treatment | 0 |

TEST EXAMPLE 2

The emulsifiable concentrate of each test compound formulated according to Formulation example 1 was diluted with water, and 20 ml of the resulting aqueous dilute liquor was mixed with 500 g of soil to make the concentration of active ingredient in soil 1 ppm. The soil was then placed in a polyethylene cup of 12 cm in diameter and 8 cm high, and five pieces of cut carrot were buried as bait. At the same time, four third instar larvae of cupreous chafer (*Anomala cuprea* Hope) were liberated in the cup.

Seven days after liberation, the number of the dead and alive of the larvae was examined to obtain mortality (%). The result is shown in Table 4.

TABLE 4

| Test Compound | Mortality (%) |
| --- | --- |
| (8) | 100 |
| (10) | 100 |
| (11) | 100 |
| (A) | 43.8 |
| No treatment | 0 |

TEST EXAMPLE 3

A polyethylene cup of 12 cm in diameter and 8 cm high was filled with soil infested with root-knot nematodes (Meloidogyne sp.), and three tomato seedlings at three- to four-leaf stage were planted. One day after planting, the emulsifiable concentrate of each test compound formulated according to Formulation example 1 was diluted with water to make the concentration of active ingredient 500 ppm, and the soil was drenched with 30 ml of the resulting aqueous dilute liquor. Eighteen days after drenching, the infection state of root-knot was examined and graded as shown in Table 5 to obtain a degree of infection. The result is shown in Table 6.

TABLE 5

| Degree of insertion | State of infection |
| --- | --- |
| − | No infection |
| − to + | Slight infection |
| + | Insertion is observed, but clearly little as compared with the untreated plot. |
| + + | Much infection similar to the untreated plot. |
| + + + | Same or more infection as compared with the untreated plot. |

TABLE 6

| Test compound | Degree of infection |
| --- | --- |
| (2) | − |
| (5) | − |
| (6) | − |
| (8) | − |
| (11) | − |
| (12) | − |
| (13) | − |
| (A) | − to + |

What is claimed is:

1. A dithiolphosphoric acid ester of the formula

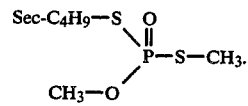

* * * * *